United States Patent [19]

Saida

[11] Patent Number: 4,822,737

[45] Date of Patent: Apr. 18, 1989

[54] PROCESS FOR PRODUCING ETHANOL BY FERMENTATION

[75] Inventor: Toyoyasu Saida, Fujisawa, Japan

[73] Assignee: Research Association for Petroleum Alternatives Development, Tokyo, Japan

[21] Appl. No.: 662,466

[22] Filed: Oct. 18, 1984

[30] Foreign Application Priority Data

Oct. 21, 1983 [JP] Japan .................. 58-197328

[51] Int. Cl.[4] .................. C12P 7/10; C12P 7/08; C12P 7/06
[52] U.S. Cl. .................. 435/162; 435/161; 435/255; 435/942
[58] Field of Search ............... 435/161, 162, 942, 255

[56] References Cited

U.S. PATENT DOCUMENTS 2,390,779 12/1945 Cornwell ..................... 435/161
4,326,036 4/1982 Hayes ......................... 435/161

OTHER PUBLICATIONS

Toledo, R. T., *Program & Abstracts: 44th Annual IFT Meeting*/Anaheim, Jun. 10-13, 1984.
Toledo, Romeo, T., *Food Technology*, 38(12), pp. 92-96 (Dec. 1984).
Kirk-Othmer *Encyclopedia of Chemical Technology*, vol. 15, 3rd edition, (1981), pp. 112-114.
Perry's *Chemical Engineers' Handbook*, 6th Edition, (1984), pp. 27-28, (McGraw Hill Co. Customer Service gave us Jul. 1984, as the copyright date.)
Kloss, Masters Thesis, *Reverse Osmosis Separation of Compounds Involved in Fermentation*, Univ. of Georgia, (1982), pp. 1-114.
Dictionary of Scientific and Technical Terms, McGraw-Hill, pp. 1054 and 1259, 1974.
Kirk-Othmer's Encyclopedia of Chemical Technology, third ed., vol. 15, pp. 116-117, published 1978.
Perry's Chemical Engineers' Handbook, Sixth Edition, McGraw-Hill 17-18, 17-19, 17-22, 17-23, 1984.

Primary Examiner—Charles F. Warren
Assistant Examiner—Carolyn S. Greason
Attorney, Agent, or Firm—Flynn, Thiel, Boutell & Tanis

[57] ABSTRACT

Ethanol is prepared from a saccharide such as glucose by a fermentation process. The efficiency of the fermentation is improved by feeding a residual fermented liquid obtained from an evaporator used to vaporize ethanol to a reverse osmosis unit, and then subjecting the residual liquid to reverse osmosis to remove water therefrom. This residual liquid is then recycled to the original fermenter, or to a second fermenter having a smaller volume than the first fermenter.

19 Claims, 3 Drawing Sheets

PROCESS FOR PRODUCING ETHANOL BY FERMENTATION

This invention relates to a process for producing ethanol by fermentation. More particularly, this invention relates to a fermentation process for the production of ethanol in which ethanol is separated from a fermented liquid by vaporization, then water is removed from the remaining fermented liquid by means of reverse osmosis whereby to increase the concentration of the saccharides in the remaining fermented liquid, and the resulting concentrated fermented liquid is recycled to a fermenter to undergo further fermentation. Highly concentrated ethanol is recovered as a product. A low concentration of ethanol and a high concentration of saccharides are maintained in the fermenter and thus the fermentation is performed efficiently.

It is well known in prior art processes that a highly concentrated ethanol solution can be produced through separation and recovery of ethanol by vaporization from a fermented liquid which has been fermented to a desired ethanol concentration. However, the absolute quantity of ethanol in the highly concentrated aqueous ethanol solution obtained by the prior art processes is only approximately one-half of the total quantity of the ethanol in the fermented liquid removed from the fermenter, and the remaining one-half of the total ethanol can only be obtained in the form of an extremely dilute aqueous solution containing 1–4% by weight of ethanol. Furthermore, the fermenter employed in these prior art processes is a single vessel functioning by effecting complete mixing. Consequently, in order to increase the degree (%) of conversion of saccharides (generally glucose and/or sucrose), the starting substrate for the fermentation, to ethanol, it is necessary to keep the saccharide concentration in the fermenter at a low level, as a result of which the rate of fermentation, that is, the speed of the fermentation reaction, is inevitably reduced. This is one of the factors that decreases the rate of fermentation.

Accordingly, it is a common practice to maintain the ethanol concentration in the fermenter at a low level in order to avoid the aforementioned disadvantage. The ethanol fermentation is hindered if a high concentration of ethanol is present and the rate of ethanol production is thereby radically decreased. However, although a solution of the problem of improving the degree of conversion of glucose to ethanol is attained by reducing the ethanol concentration in the fermenter, this does not improve the rate of fermentation in relation to the concentration of glucose in the fermenter. The latter is another factor that decreases the rate of fermentation. The rate of fermentation to produce ethanol is slow when the concentration of glucose in the fermenter is low.

To solve this problem, a process has been proposed in which several fermenters are arranged in series. The first fermenter of the series is operated at a high glucose concentration, and the last fermenter in the series is run at a low glucose concentration, thereby improving the degree of ethanol conversion as well as the fermentation rate. However, as compared to a fermenter which is a single vessel that functions by complete mixing as described above, the series of fermenters in this prior art process is improved in that the total fermenter volume is decreased, but is not improved as to the overall efficiency of the equipment, and this prior art process is complex because of the need for a multiplicity of fermenters.

Figure 1:
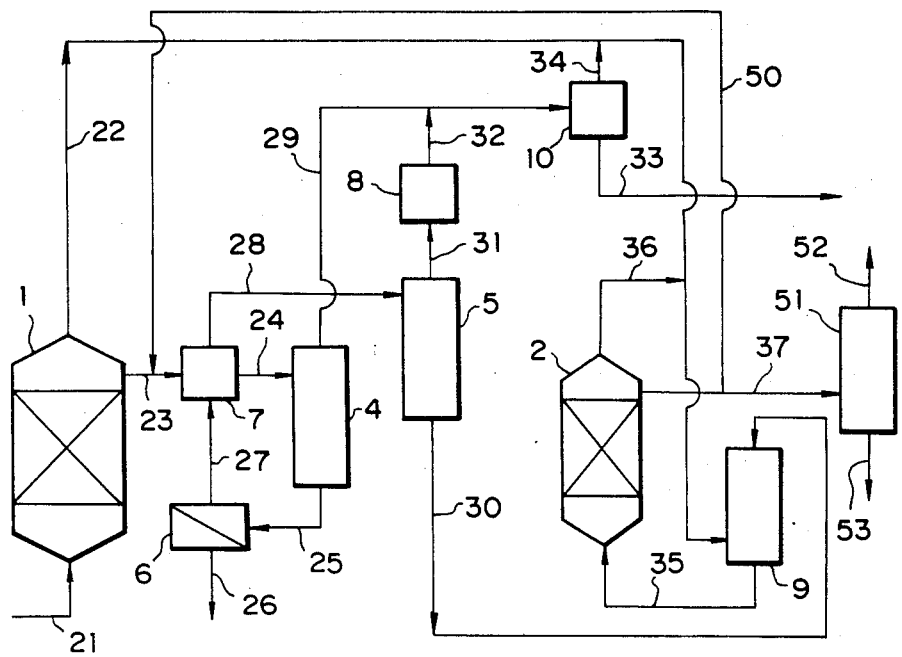
FIG. 1 is a schematic flow diagram of the process of the invention using a pair of fermenters containing immobilized microorganisms for fermentation.

It is an object of the present invention to provide a process for producing a large amount of highly concentrated ethanol in a fermenter of very small volume by markedly increasing the proportion of highly concentrated ethanol that is recovered, to wit, the amount of ethanol that is recovered at a high ethanol concentration in relation to the total ethanol that is recovered.

It is a further object of the invention to improve the rate of fermentation by increasing the glucose (saccharide) concentration in the fermenter.

More specifically, the present invention provides a process for producing ethanol by fermentation wherein a fermented liquid extracted from a fermenter, which liquid contains substantially no fermentation microorganisms, is subjected to vaporization whereby ethanol in this fermented liquid is vaporized, separated and recovered. The process of the invention is characterized in that a fermented liquid discharged from a first evaporator is fed to a reverse osmosis unit wherein water is separated from the fermented liquid discharged from the first evaporator. The fermented liquid discharged from the reverse osmosis unit is greatly reduced in water content and it is recirculated to the original fermenter or another fermenter for renewed fermentation.

According to the process of the invention, the amount of ethanol separated and recovered by vaporization is increased so that the amount of ethanol recycled to the fermenter is decreased. Moreover, the concentration of the saccharides in the recycled fermented liquid is increased by the reverse osmosis treatment. As a result, the disadvantages of the prior art processes are ameliorated. The present invention provides a fermentation process for producing ethanol with an extremely high efficiency.

A variety of fermenter units can be used in the practice of the present invention. These units include:

(1) fermenters which use a fixed or fluidized bed of an immobilized microorganism for fermentation;

(2) fermenters having a fluidized bed which comprises a flocculent microorganism;

(3) fermenters provided with an apparatus whereby a flocculent fermentation microorganism in the fermented liquid extracted from the fermenter is precipitated, separated and recycled to the fermenter;

(4) fermenters divided into sections including a section for precipitating a flocculent microorganism; and (5) fermenters provided with an apparatus whereby a suspended fermentation microorganism in the fermented liquid extracted from the fermenter is centrifuged, filtered or precipitated out and then recycled to the fermenter.

Although all of the foregoing fermenters can be used in the practice of the present invention, the fermenter (1) which utilizes an immobilized or fixed microorganism is simplest and entails little risk of contamination, and thus, this fermenter is preferred in practice. As a second choice, fermenters which use a flocculent microorganism and have means for retaining the microorganism within the fermenter can also be used advantageously.

The first evaporator comprises an apparatus for vaporizing ethanol at a selected temperature and pressure. If this first evaporator is operated at a reduced pressure (vacuum), it is necessary to install further equipment for pressurizing the vaporized ethanol so as to condense it by water cooling or a similar method, or to use a refrigerator for cooling the vaporized ethanol to condense it in a recovery condenser. If this is not done, it will become difficult to condense and recover the vaporized ethanol under reduced pressure. If the evaporator is operated at a reduced pressure, a low level heat source is sufficient for effecting the vaporization of the ethanol.

If the first evaporator is instead run at a high pressure, the vaporized ethanol can be condensed easily by cooling means, such as air cooling or water cooling, and a high degree of ethanol recovery can be obtained. In this case, it is necessary to use a high level heat source for the vaporization of ethanol and a pressure vessel for carrying out the vaporization therein.

The first evaporator is preferably operated at an absolute pressure in the range of 0.8 to 10 atm, most preferably 1 to 3 atm. The first evaporator is operated at a boiling point of the fermented liquid supplied thereto. The boiling point is dependent on the operating pressure, composition of the fermented liquid, etc. Preferably, the operating temperature is 75°–105° C. under the pressure of 0.8–1.2 atm abs. and 95°–180° C. under the pressure of 1.2–10 atm abs. A conventional evaporator or a multi-stage distillation column can be used as the first evaporator. If a multi-stage distillation column is used, the fermented liquid supplied thereto is fed in at the top of the column and is heated at the bottom of the column. Consequently, there is obtained an ethanol vapor in substantial equilibrium with the ethanol in the fermented liquid supplied at the top of the column. If the distillation column is provided with a sufficient number of stages, the fermented liquid discharged from the bottom of the column will contain substantially no ethanol, and therefore the discharged fermented liquid will contain only saccharides and nonvolatile materials. It is not necessary or desirable to use a column that achieves total ethanol removal from the fermented liquid, in the present invention. Rather, a conventional evaporator or a distillation column having about 10 stages is preferably used for practicing the process of the present invention, because substantially total recovery of ethanol in the first evaporator will decrease the effectiveness of the subsequent reverse osmosis step and the second evaporation step using a second evaporator. In addition, if all of the ethanol is to be recovered in the first evaporator, the complexity of the first evaporator must be greatly increased as compared to the conventional evaporator or distillation column having about 10 stages that is preferably used in the present invention.

The reverse osmosis unit contains a semi-permeable reverse osmosis membrane which can reject alcohols and fermentable saccharides but is permeable to water. If the reverse osmosis unit is only capable of treating a fermented liquid which is free of suspended solids, it is necessary to provide an apparatus for removing such solids in advance of the reverse osmosis unit. This is necessary because even when the fermenter employs an immobilized microorganism, a small amount of the immobilized microorganism unavoidably leaks out of the fermenter. Also, the feed liquid for the fermentation initially contains a very small amount of solids. The reverse osmosis unit used in the present invention is preferably one which is capable of treating a fermented liquid which contains a small amount of micro-organisms and/or other suspended solids.

A reverse osmosis semi-permeable membrane such as HR membrane, a product of De Danske Sukkerfabrikker Co. of Denmark, or PEC-1000, a product of Toray Co. of Japan, is preferably employed in the reverse osmosis unit. Since the aforementioned HR membrane is also heat resistant, it is possible to feed a fermented liquid at a relatively high temperature from the first evaporator to the reverse osmosis unit which utilizes said membrane, with or without an advance step of slightly cooling the high temperature fermented liquid. The velocity at which water permeates through the reverse osmosis membrane, per unit area of the reverse osmosis membrane, increases at higher temperatures, and it is thus advantageous to feed the fermented liquid to the reverse osmosis unit at a relatively high temperature. The permeating velocity through the reverse osmosis membrane also increases as the pressure of the fermented liquid fed into the reverse osmosis unit increases. In addition, the degree of concentration of ethanol and saccharides in the fermented liquid being subjected to reverse osmosis also increases with increasing pressure. This is because (1) permeating velocity of water per unit area of the reverse osmosis membrane is proportional both to the difference between the pressure of feed liquid and the pressure of the permeated liquid and to the difference of osmotic pressure of the feed liquid and the permeated liquid and (2) the permeation velocities of ethanol and saccharides per unit area of the reverse osmosis membrane are virtually unrelated to those pressures mentioned in (1). The fermented liquid is generally supplied to the reverse osmosis unit at a pressure of 50 to 100 atm abs. By the reverse osmosis step, water is removed from the fermented liquid, because water permeates the reverse osmosis membrane due to hydraulic pressure. The residual fermented liquid discharged from the first evaporator typically contains 90–99 wt. % water. After reverse osmosis, the water content is preferably 80 wt. % or less, particularly 70 to 90 wt. %.

The fermented liquid discharged from the reverse osmosis unit, having an increased concentration of ethanol and saccharides, is then fed into a second evaporator. The second evaporator is preferably operated at a temperature slightly lower than the optimum fermentation temperature of the fermenter. This prevents the temperature in the subsequent fermentation step within the fermenter from increasing excessively above the optimum fermentation temperature due to the heat of fermentation generated within the fermenter. The fermented liquid discharged from the second evaporator is recirculated to the original fermenter or is circulated to another fermenter to resume the fermentation process. This arrangement utilizes the heat of fermentation in the second evaporation step, which heat was previously discarded to cooling water, in conventional ethanol fermentation processes.

The optimum fermentation temperature in the fermenter (s) varies depending on the particular fermentation microorganisms employed, but a range of 25° to 40°

C. is generally preferred. Higher fermentation temperatures are preferred, and thus the preferable microorganism for fermentation is heat resistant. As this microorganism, any known yeast or bacterium employed for fermentation to produce ethanol can be used, such as the yeast disclosed in U.S. Pat. No. 2,440,925, the contents of which are expressly incorporated by reference herein. More generally, any microorganism of the genus Saccharomyces useful for producing ethanol by fermentation can be employed. Such strains of Saccharomyces cerevisiae as bakers yeast can also be generally used.

The second evaporator is most preferably operated at a temperature of from 25° to 65° C. In order to sufficiently transfer the ethanol in the fermented liquid supplied to the second evaporator to a vapor phase at a temperature in this range, it is necessary to reduce the pressure in the second evaporator, preferably to less than 1 atm, most preferably to a pressure in the range of 20 to 200 mmHg.

The fermented liquid discharged from the second evaporator has been sufficiently cooled and has a low ethanol concentration. It is preferable to use this liquid as an absorbent to absorb and recover the ethanol contained in the effluent gas from the original (first) fermenter, which gas mainly comprises carbon dioxide and to absorb and recover ethanol contained in the effluent gas from the condenser. After the fermented liquid has absorbed ethanol in this fashion, it is recirculated to the first fermenter or another fermenter. As a result of these measures, the ethanol concentration in the fermenter(s) can be maintained at a relatively low level, preferably 8% by weight or less. On the other hand, the concentration of saccharides in the fermenter(s) is maintained at a high level, so that the rate of fermentation is tremendously increased. It therefore becomes possible, according to the invention, to recover the greater part of the ethanol produced as a concentrated ethanol solution while maintaining the efficiency of the fermenter at an extremely high level.

Several embodiments of the process of the present invention are described below in further detail and are illustrated in the drawings.

FIG. 1 is a flow diagram of an embodiment of the present invention wherein an immobilized microorganism fermenter is used. In FIG. 1, an aqueous solution containing fermentable saccharide(s), such as glucose, is fed through line 21 to a first fermenter 1 containing a bed of an immobilized fermentation microorganism. Ethanol and carbon dioxide are thereby produced by fermentation. The greater part of the gas generated in the first fermenter 1, which gas mainly comprises carbon dioxide, is discharged therefrom through a line 22. A fermented liquid which has been fermented to a desired ethanol concentration is discharged from the first fermenter 1 and fed through a line 23 to a heat exchanger 7. The fermentation liquid from the fermenter 1 is preheated in the heat exchanger 7 by heat exchange with the concentrated fermented liquid that is discharged from the reverse osmosis unit 6 and is supplied to the heat exchanger 7 through a line 27. The fermented liquid from the fermenter 1 is then fed into the first evaporator 4 through a line 24. The first evaporator 4 is a distillation column having several stages, and is provided with a drum which is heated by steam at its bottom.

The greater part of the ethanol and noncondensible gases, such as carbon dioxide dissolved in the fermented liquid fed to the first evaporator 4 are transferred to the vapor phase in the first evaporator 4 and are discharged through a line 29. The remaining fermented liquid, from which ethanol and noncondensible gases have been removed, is discharged from the bottom of the first evaporator 4 and is fed into the reverse osmosis unit 6 through the line 25.

Substantially only water is separated from the fermented liquid supplied to the reverse osmosis unit 6 by operation of the reverse osmosis semi-permeable membrane. The separated water is discharged outside of the system through the line 26. The remaining fermented liquid from which water has been separated, thereby contains an increased concentration of ethanol and solids (soluble solids plus suspended solids), such as saccharides. This concentrated fermented liquid is fed via the line 27 through the heat exchanger 7 wherein it is cooled by heat exchange with the fermented liquid discharged directly from the first fermenter 1. After being cooled in the heat exchanger 7, the fermented liquid is fed into a second evaporator 5 through a line 28.

The second evaporator 5 can be an apparatus similar to the first evaporator 4. The second evaporator 5 is generally operated under heating at a reduced pressure (vacuum) so that the temperature of the fermented liquid discharged from its bottom is slightly lower than the fermentation tempeature in the subsequent second fermenter 2 containing immobilized microorganisms for fermentation. As a result, the second fermenter 2 is operated at the approximate desired fermentation temperature due to the heat of fermentation evolved therein.

The fermented liquid discharged from the second evaporator 5 is fed to a washing column 9 through a line 30. The effluent gas from the second evaporator 5 is fed through a line 31 to a vacuum pump 8, wherein it is pressurized. Thereafter, the pressurized effluent gas is fed through a line 32 which merges with the line 29 wherein the effluent gas from the second evaporator 5 is combined with the effluent gas from the first evaporator 4. The combined effluent gases are then fed to a condenser 10 wherein ethanol in the combined effluent gas is condensed, and the condensed liquid ethanol is discharged through a line 33 in the form of a concentrated aqueous ethanol solution, the desired product. The noncondensible gases discharged from the condenser 10 are fed through a line 34 to the line 22 wherein these gases are combined with the effluent gas from the first fermenter 1. The effluent gas from the second fermenter 2 is discharged through a line 36 to the line 22 and is combined with the gaseous mixture of the effluent gas from the first fermenter 1 and the noncondensible gases from the condenser 10. The resulting gaseous mixture is fed through the line 22 into the washing column 9.

The fermented liquid from the second evaporator 5 which has been fed into the washing column 9 absorbs and recovers ethanol contained in the gaseous mixture fed into the washing column 9 through the line 22. The fermented liquid is then discharged from the washing column 9 and fed through the line 35 into the second fermenter 2 containing immobilized fermentation microorganisms. The amount of fermented liquid fed to the second fermenter 2 is less than the amount of the liquid that was fed to the first fermenter 1, the difference being the amount of water that was separated in the reverse osmosis unit 6 and the amount of liquid that was evaporated in the first and second evaporators 4 and 5. The diameter of the second fermenter 2 may accordingly be correspondingly smaller than the diameter of the first fermenter 1. In such a case, if the height of the second fermenter 2 is equal to the height of the first fermenter 1, the ratio of the volume of the first fermenter 1 to the volume of the second fermenter 2 will equal the ratio of the square of the radius of the first fermenter 1 to the square of the radius of the second fermenter 2. The ratio of the amount by weight per hour of the first fermented liquid discharged from the first fermenter to the amount by weight per hour of the second fermented liquid discharged from the second fermenter is preferably at least 10, particularly 12 to 15.

After the fermented liquid in the second fermenter 2 has been fermented to a predetermined ethanol concentration, this fermented liquid is discharged through a line 37. This fermented liquid may be partially or completely branched through a line 50 to the line 23, wherein the fermented liquid from the second fermenter 2 is combined with the fermented liquid from the first fermenter 1. Alternatively, if the saccharide concentration in the fermented liquid from the second fermenter 2 has been reduced to a negligible level, this fermented liquid may be fed through the line 37 to a subsequent distillation column 51 in which this fermented liquid is distilled to form a concentrated aqueous ethanol solution which is condensed from vapor discharged through the line 52 and a fermentation waste liquid free of ethanol containing nutritious salts, nonfermentable saccharides, a small amount of yeast, and the like which is discharged through the line 53. The aqueous ethanol solution thus obtained can be combined with the aqueous ethanol solution obtained from the line 33, and the combined product can be subjected to succeeding treatments, such as dewatering.

Figure 2:
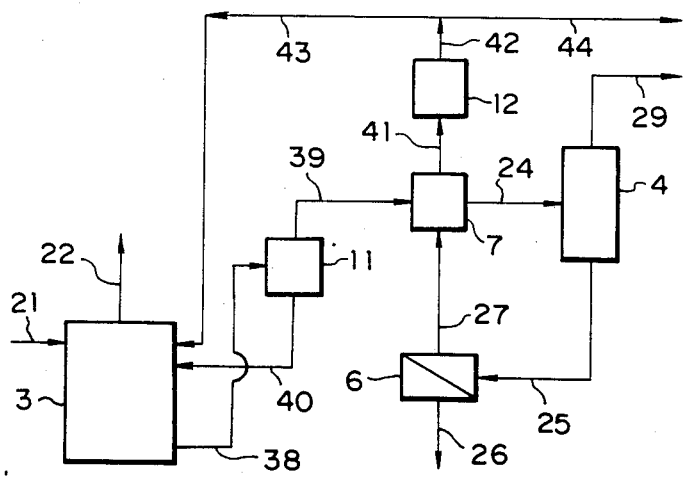
FIG. 2 is a schematic flow diagram of a second embodiment of the process of the invention wherein a single fermenter is used.

FIG. 2 illustrates a flow diagram for an embodiment of the process of the invention wherein only a single fermenter is used. In FIG. 2, a starting material for fermentation, that is, a feed liquid comprising saccharides and water, is supplied through a line 21 into a fermenter 3 wherein ethanol and $CO_2$ are produced. The greater part of the gas evolved in the fermenter 3 is discharged therefrom through a line 22. Ethanol contained in the gas evolved from the fermenter 3 is recovered in the same manner as described above in connection with FIG. 1. In the fermenter 3, fermentation microorganisms are suspended in the fermentation liquid by stirring. The fermented liquid containing ethanol produced by fermentation is fed together with the fermentation microorganisms through a line 38 to a separator 11. The separator 11 is a precipitation separator if a flocculent microorganism is being used, whereas it is a continuous centrifugal separator if a suspended microorganism is being used.

The microorganisms separated from the fermented liquid in the separator 11 are recycled to the fermenter 3 through a line 40. The fermented liquid free of the microorganisms is discharged through a line 39 and fed into a heat exchanger 7 wherein it is heated by undergoing heat exchange with the concentrated fermented liquid discharged from the reverse osmosis unit 6. The thus-heated fermented liquid is fed into a first evaporator 4 through a line 24. Ethanol and a noncondensible gas vaporized in the evaporator 4 are discharged through a line 29, whereas the fermented liquid withdrawn from the first evaporator 4 is fed to the reverse osmosis unit 6 through the line 25.

Substantially only water is extracted from the fermented liquid in the reverse osmosis unit 6, and this water is discharged from the system through a line 26. The fermented liquid thus concentrated in ethanol and solids, such as saccharides, is fed through a line 27 to the heat exchanger 7 and is cooled therein. The fermented liquid is then fed through a line 41 to a cooler 12, wherein the fermented liquid is cooled to a temperature slightly lower than the fermentation temperature of the fermenter 3. The fermented liquid can then be recycled to the fermenter 3 through the lines 42 and 43. A cooling coil or jacket may be installed in the fermenter 3 for cooling the fermented liquid from the line 43, in place of the cooler 12. In order to prevent nonfermentable saccharides from accumulating in the fermenter 3, part of the fermented liquid discharged from the cooler 12 through the line 42 may be branched to the line 44 and discharged outside of the system.

The fermenter 3 is a single fermenter, and water in the starting fermentation liquid supplied thereto through the line 21 is continuously discharged through the lines 29 and 26 and partially discharged through the line 44 outside of the system, so that the saccharide concentration in the fermenter 3 is maintained at a high level. The ethanol produced by fermentation is continuously discharged through the line 29 as a vapor having a high ethanol concentration, whereby the ethanol concentration in the fermenter 3 is maintained at a low level. Thus, both the rate of fermentation and the yield of ethanol through fermentation can be greatly improved.

In the following examples and comparative examples, amounts are given in kilograms per hour (kg/h) or liters per hour (l/h). It should be understood that these units actually represent amounts per unit time.

EXAMPLE 1

Figure 3:
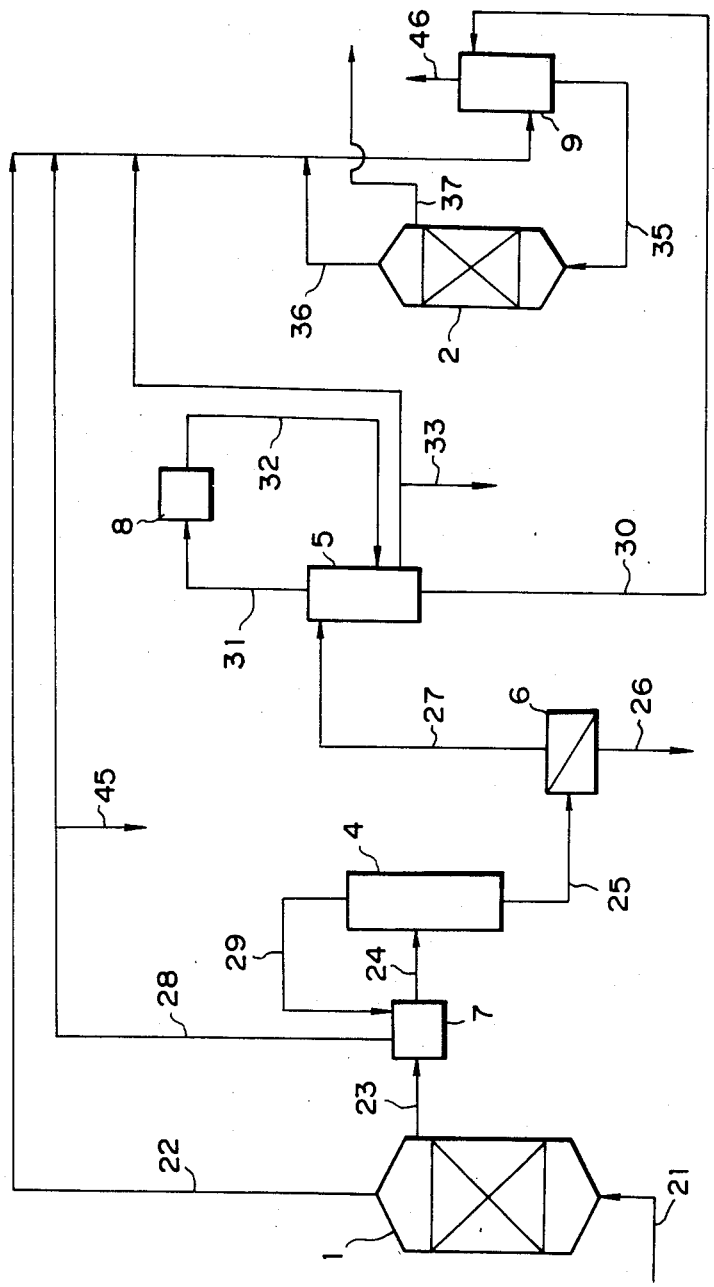
FIG. 3 is a schematic flow diagram for the process described in Example 1.

Referring to FIG. 3, 2000 liters per hour of an aqueous feed liquid (cane sugar juice) containing 10 wt. % of fermentable saccharides (mainly sucrose) and other nutritious substances for microorganisms was fed into a first fermenter 1 through a line 21. The first fermenter 1, which utilized an immobilized fermentation microorganism, was packed in advance with 2200 liters of immobilized yeast. The yeast employed was immobilized Saccharomyces cerevisiae (bakers yeast) on a calcium alginate carrier, and was in the form of beads. The fermenter 1 was maintained at 35° C., and 86.9 kg/h of ethanol was produced at its top portion. 0.2 kg/h of the produced ethanol was discharged from the fermenter in vapor form through the line 22 together with 83.2 kg/h of gaseous carbon dioxide that was evolved in the fermenter. The remainder of the fermented liquid, comprising 86.7 kg/h of ethanol mixed with 30.0 kg/h of residual fermentable saccharides, was fed through the line 23 into the heat exchanger 7, wherein the fermented liquid was preheated to 92° C. This fermented liquid contained 4.53 wt. % ethanol and 1.57 wt. % residual fermentable saccharides.

This fermented liquid was fed from the heat exchanger 7 through the line 24 into the first evaporator 4. The first evaporator 4 was a distillation column filled with wire net packing which correspond to five theoretical distillation stages, and was heated by a steam reboiler and operated at 95° C. A vapor comprising 76.5 kg/h of ethanol and 136.6 kg/h of water was discharged from the top of the evaporator 4 and was fed through the line 29 into the heat exchanger 7. The vapor was cooled and condensed in the heat exchanger 7 to form a condensate containing 35.9 wt. % of ethanol.

The liquid discharged from the bottom reboiler of the evaporator 4, which liquid was reduced in amount relative to the starting aqueous solution, was fed at a rate of 1701.6 kg/h through a line 25 to the reverse osmosis unit 6 which was operated at a pressure of 60 atmospheres. The reverse osmosis unit 6 was a DDS-type 20 module provided with DDS-HR99 reverse osmosis membrane, a booster recycle pump and a recycle liquid cooler. In the reverse osmosis unit, a permeate liquid comprising 1501.6 kg/h of water was separated from 200 kg/h of a concentrate containing 5.1 wt. % of ethanol and 15 wt. % of fermentable saccharides, which concentrate was at a temperature of 60° C. This concentrate was fed to a second evaporator 5 through a line 27, wherein it was heated to 30° C., at a pressure of 32 mmHg, whereby to generate a vapor consisting of 7.8 kg/h of ethanol and 44.4 kg/h of water. This vapor was fed through a line 31 to a vacuum pump 8 wherein it was pressurized to atmospheric pressure. This vapor was then fed through a line 32 which included a heating coil installed in the second evaporator 5. The heating coil served to heat the second evaporator 5 and correspondingly caused the vapor in the line 32 to condense to form a condensate containing 15 wt. % of ethanol. A residual solution containing 2.4 kg/h of ethanol, 30.0 kg/h of fermentable saccharides and 115.4 kg/h of water was discharged from the bottom of the evaporator 5 through a line 30 and was fed to a washing column 9 as an absorbent liquid.

The aqueous solution which absorbed ethanol in the washing column 9 was fed to a second fermenter 2 through a line 35. The second fermenter 2 was packed with 350 liters of the same immobilized yeast beads as those used in the fermenter 1. In the second fermenter 2, a gaseous mixture comprising 9.1 kg/h of carbon dioxide, 0.05 kg/h of ethanol and 0.5 kg/h of water was discharged from the top of the fermenter 2, and a fermented liquid containing 12.1 kg/h of ethanol, 11.4 kg/h of fermentable saccharides, and 115.8 kg/h of water was produced and discharged through a line 37.

Effluent gases from the first fermenter 1, heat exchanger 7, vacuum pump 8 and second fermenter 2 were fed through lines 22, 28, 32 and 36, respectively, which lines were combined so that the resulting gaseous mixture was fed to the washing column 9. The remaining noncondensible gases, having been stripped of ethanol in the washing column 9, were discharged from the system through the line 46. Liquid ethanol was subsequently collected through lines 45 and 33 after being condensed in the heat exchanger 7 and line 32, respectively. The overall process produced 96.4 kg/h of ethanol having an average concentration of 23.8 wt. %, resulting in an overall yield of 94.3%.

The amounts of nutritious salts, solid yeast leaked from the fermenters and other such ingredients are included in the amounts of water specified above.

COMPARATIVE EXAMPLE 1

The same ethanol production reaction as described for Example 1 above was carried out by the Reuse yeast process (K. Rosen, Process Biochemistry 5, p25(1978)). This process uses three fermenters connected in series. Each of these fermenters required 3200 liters of effective volume. Moreover, the ultimate average ethanol concentration obtained was as low as 5.1 wt. % because the starting saccharide solution was not concentrated. Even if the starting saccharide solution was previously concentrated, as can be done by subjecting the starting saccharide solution to reverse osmosis, the ultimate average ethanol concentration in the aqueous ethanol product solution would be at most 10 wt. % due to the limited activity of the yeast.

COMPARATIVE EXAMPLE 2

The same fermentation reaction as described in Example 1 was carried out using a flash fermentation unit except that the reverse osmosis unit was not employed. The amount of solution treated in the second evaporator was as high as 1700 kg/h, an enormous amount as compared to the corresponding amount of 200 kg/h in Example 1. The capacity of the second evaporator and the associated vacuum pump needed to be increased correspondingly. Furthermore, the ethanol concentration in the condensate obtained from the second evaporator was only 1.7 wt. %, whereas the residual solution was discharged from the bottom of the evaporator in an amount as large as 1233.3 kg/h. This residual solution comprised 2.2 kg/h of ethanol, 29.1 kg/h of fermentable saccharides (2.36 wt. %) and 1202 kg/h of water.

In this type of process, the design of the second fermenter containing immobilized microorganisms is considerably more difficult than in the present invention because its column diameter must be made sufficiently large so that the liquid velocity in the column does not become excessively high. The concentration of ethanol in the fermented liquid thus obtained in the second fermenter is generally only about 1 wt. %.

COMPARATIVE EXAMPLE 3

Even when the starting solution fed to the first fermenter is previously concentrated by a reverse osmosis unit or other means, it is necessary to operate the first fermenter to obtain an ethanol concentration of about 5 wt. % in the fermented liquid discharged from the outlet of the first fermenter. This is necessary in order to carry out flash fermentation, because if the fermenter is operated at a higher ethanol concentration than 5 wt. %, the size of the fermenter must be increased, and thereby the removal of the heat of fermentation or at least the effective utilization thereof becomes more difficult. Consequently, excessive concentration of the feed solution leads to a lower degree of conversion of saccharides to ethanol in the first fermenter. The concentration of the feed solution supplied to the first fermenter is therefore limited.

For example, when a feed liquid containing 15 wt. % fermentable saccharides concentrated by a reverse osmosis unit was fed to the first fermenter, the fermented liquid discharged from the first fermenter was composed of 62.3 kg/h of ethanol (concentration 4.9 wt. %) , 77.7 kg/h of fermentable saccharides and 1131.9 kg/h of water. The gas evolved by fermentation in the first fermenter comprised 59.8 kg/h of carbon dioxide, 0.165 kg/h of ethanol and 1.41 kg/h of water. The first fermenter was filled with 1600 liters of immobilized yeast. In the first evaporator, the fermented liquid was separated into a vapor comprising 55.6 kg/h of ethanol (concentration 35.9 wt. %) and 99.3 kg/h of water, and a residual liquid consisting of 6.7 kg/h of ethanol (concentration 0.6 wt. %), 77.7 kg/h of fermentable saccharides and 1032.6 kg/h of water. The residual liquid discharged from the first evaporator was further separated into a vapor comprising 5.2 kg/h of ethanol (concentration 1.71 wt. %) and 301.3 kg/h of water, and a further residual liquid consisting of 1.5 kg/h of ethanol (concentration 0.185 wt. %), 77.7 kg/h of fermentable saccharides and 731.3 kg/h of water. The second fermenter was packed with 1200 liters of immobilized yeast, and the ethanol concentration of the fermented liquid discharged from the outlet of the second fermenter was 4.57 wt. %.

The total amount of immobilized yeast packed in the first and second fermenters was 2800 liters, a larger amount than employed in Example 1. This was due to the proportion of the load on the second fermenter, the second fermenter being inferior in productivity to the first fermenter, which proportion was larger than the corresponding proportion of load on the second fermenter in Example 1. Although the ethanol yield in this Comparative Example was 94.3%, the same as in Example 1, the ultimate average concentration of 96.4 kg/h of ethanol obtained by this comparative process was only 7.75 wt. %.

EXAMPLE 2

Figure 4:
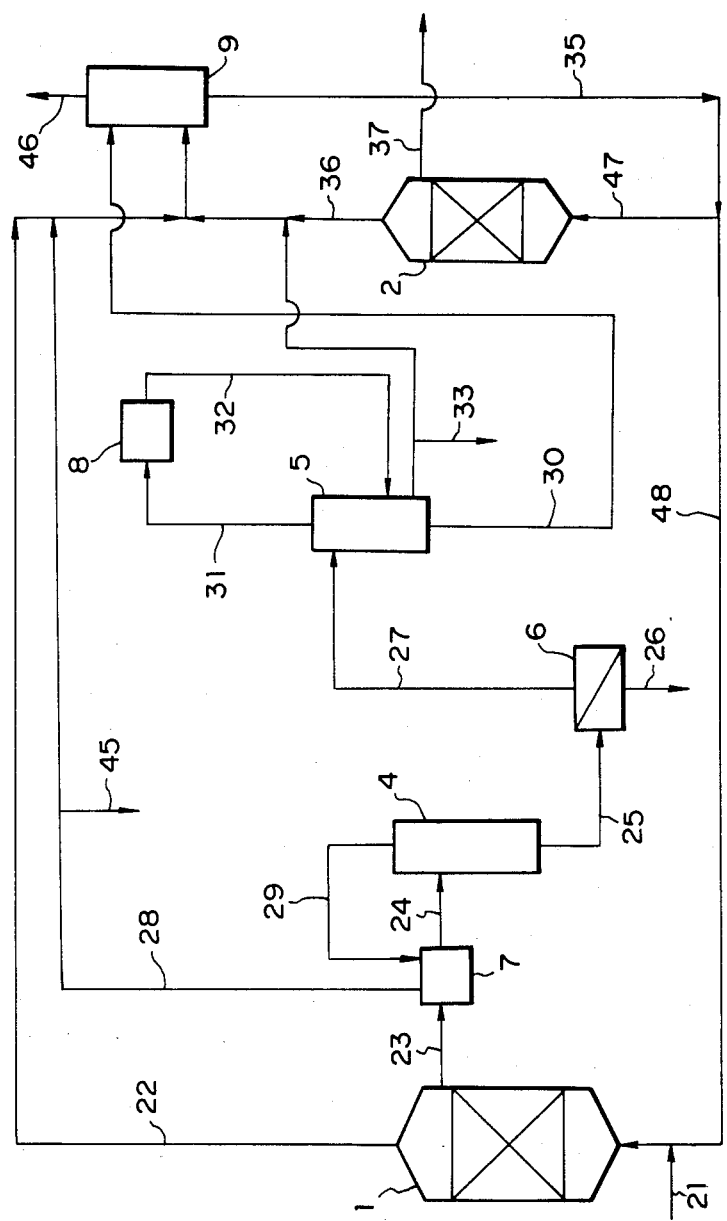
FIG. 4 is a schematic flow diagram of the embodiment of the invention described in Example 2.

The same cane juice feed liquid as used in Example 1 was preconcentrated to a concentration of 15 wt. % of fermentable saccharides by a reverse osmosis unit (not shown). The thus-concentrated solution was used as the starting fermentation liquid in this Example. The fermentation was carried out using the fermentation unit schematically illustrated in FIG. 4, which unit was substantially the same as the unit described in connection with Example 1, except that the greater part of the outlet solution from the washing column 9 was recirculated through a line 48 to the first fermenter 1, and the remaining smaller part of this solution was fed through a line 47 to the second fermenter 2. The starting fermentation liquid was fed through the line 21 to the line 48 and combined with the residual liquid recycled from the washing column 9.

The following table describes the results of Examples 1 and 2. The flow rates for the fermentable saccharides, ethanol, carbon dioxide and water were measured in the various flow lines 21 through 48.

from the vaporized ethanol, a residual fermented liquid comprising liquid ethanol, unfermented saccharide and water;

feeding the residual fermented liquid comprising liquid ethanol, unfermented saccharide and water from said evaporator to a reverse osmosis unit;

subjecting said residual fermented liquid to reverse osmosis in said reverse osmosis unit to remove water therefrom and thereby obtain a concentrated fermented liquid containing a higher concentration of saccharide and ethanol than said residual fermented liquid; and then feeding said concentrated residual fermented liquid to a fermenter wherein fermentation of said saccharide is taking place.

2. A process as claimed in claim 1, wherein said saccharide comprises glucose and/or sucrose, and said microorganism is a strain of Saccharomyces cerevisiae immobilized on carrier beads.

3. A process as claimed in claim 1, wherein the water concentration of said residual fermented liquid being fed from said evaporator to said reverse osmosis unit is in the range of about 90 to 99 wt. %, and the concentration of water in said concentrated fermented liquid after being subjected to reverse osmosis is in the range of 70 to 90 wt. %.

4. A process for the preparation of ethanol by fermentation, which comprises:

feeding a liquid comprising a saccharide and water into a first fermenter which contains a microorganism effective to metabolize said saccharide to form ethanol therefrom and fermenting said saccharide in said first fermenter to form a first fermented liquid comprising ethanol, residual saccharide and water;

feeding said first fermented liquid into a first evaporator and vaporizing ethanol from said first fermented liquid in said first evaporator;

cooling said ethanol vaporized in said first evaporator to condense said ethanol, and recovering the thus-formed liquid ethanol;

TABLE

| (Constituents) | 21 | 22 | 23 | 25 | 26 | 27 | 29 | 30 | 31 | 33 | 35 | 36 | 37 | 45 | 46 | 47 | 48 |
|---|---|---|---|---|---|---|---|---|---|---|---|---|---|---|---|---|---|
| Example 1: | | | | | | | | | | | | | | | | | |
| fermentable saccharides (kg/h) | 2000 | | 30.0 | 30.0 | | 30.0 | | 30.0 | | | 30.0 | | 11.4 | | | | |
| ethanol (kg/h) | | 0.2 | 86.7 | 10.2 | | 10.2 | 76.5 | 2.4 | 7.8 | 7.8 | 2.65 | 0.05 | 12.1 | 76.5 | | | |
| $CO_2$ (kg/h) | | 83.2 | | | | | | | | | | 9.1 | | | 92.3 | | |
| $H_2O$ (kg/h) | | 1.97 | 1798.0 | 1661.4 | 1501.6 | 159.8 | 136.6 | 115.4 | 44.4 | 44.4 | 116.2 | 0.5 | 115.8 | 136.6 | 1.6 | | |
| Example 2: | | | | | | | | | | | | | | | | | |
| fermentable saccharides (kg/h) | 2150 | | 141.0 | 141.0 | | 141.0 | | 141.0 | | | 141.0 | | 11.4 | | | 33.8 | 107.2 |
| ethanol (kg/h) | | 0.25 | 87.75 | 9.0 | | 9.0 | 78.75 | 3.7 | 5.33 | 5.33 | 4.0 | 0.05 | 12.4 | 78.75 | | 1.0 | 3.0 |
| $CO_2$ (kg/h) | | 81.3 | | | | | | | | | | 11.0 | | | 92.3 | | |
| $H_2O$ (kg/h) | | 1.92 | 1486.9 | 1360.6 | 805.6 | 555.0 | 126.4 | 466.8 | 88.2 | | 467.7 | 0.6 | 111.6 | | 1.6 | 112.2 | 355.5 |

The embodiments of the invention in which an exclusive property or privilege is claimed are defined as follows:

1. In a process for the preparation of ethanol including the steps of fermenting, in a first fermenter, a saccharide in a fermentation liquid comprising said saccharide and water utilizing microorganisms effective to metabolize said saccharide to form a resulting fermented liquid containing ethanol therefrom and recovering the ethanol, the improvement which comprises:

vaporizing ethanol from the resulting fermented liquid in an evaporator and recovering separately feeding residual fermented liquid comprising ethanol, saccharide and water from said evaporator to a reverse osmosis unit and subjecting said residual liquid to reverse osmosis in said reverse osmosis unit to remove water therefrom and thereby increase the concentration of ethanol and saccharides in said residual liquid to obtain a concentrated residual liquid;

feeding said concentrated residual liquid from said reverse osmosis unit into a second evaporator and vaporizing ethanol from said concentrated residual liquid in said second evaporator;

cooling said ethanol vaporized in said second evaporator to condense said ethanol, and recovering the thus-formed liquid ethanol;

feeding said concentrated residual liquid from said second evaporator and thence through a washing column into a second fermenter which contains a microorganism effective to metabolize said saccharide to form ethanol therefrom, said second fermenter being smaller in volume and containing less of said microorganism than said first fermenter;

fermenting said saccharide in said second fermenter to form a second fermented liquid comprising ethanol, residual saccharide and water;

recovering ethanol from said second fermented liquid;

feeding gas produced in said first and second fermenters, said gas comprising carbon dioxide and ethanol, into said washing column so that ethanol in said gas is absorbed by said concentrated residual liquid; and repeating the foregoing steps to continuously produce ethanol.

5. A process as claimed in claim 4, wherein said microorganism is a strain of Saccharomyces cerevisiae.

6. A process as claimed in claim 4, further comprising heat exchanging said first fermented liquid being fed from said first fermenter to said first evaporator with said concentrated residual liquid being fed from said reverse osmosis unit, thereby heating said first fermented liquid and cooling said concentrated residual liquid.

7. A process as claimed in claim 4, further comprising heat exchanging said first fermented liquid being fed from said first fermenter to said first evaporator with gas produced in said first evaporator, thereby cooling said gas produced in said first evaporator and condensing liquid ethanol therefrom, and heating said first fermented liquid.

8. A process as claimed in claim 7, further comprising feeding gas produced in said second evaporator to a compressor and compressing said gas produced in said second evaporator, then heat exchanging said gas produced in said second evaporator with said concentrated residual liquid in said second evaporator to thereby heat said concentrated residual liquid and cool said gas produced in said second evaporator to condense liquid ethanol therefrom.

9. A process as claimed in claim 8, further comprising feeding said gases produced from said first and second evaporators, after said liquid ethanol has been condensed therefrom, into said washing column so that residual gaseous ethanol in said gases is absorbed by said residual liquid.

10. A process as claimed in claim 4, further comprising feeding a greater portion of said residual liquid from said washing column into said first fermenter and feeding a lesser portion of said residual liquid from said washing column into said second fermenter.

11. A process as claimed in claim 6, further comprising combining said second fermented liquid with said first fermented liquid before said heat exchanging step.

12. A process as claimed in claim 4, wherein said fermentation steps are conducted at a temperature of from 25° C. to 65° C., said first and second fermenters each contain a bed of immobilized microorganisms, said first evaporator is at a pressure in the range of 0.8 to 10 atm abs., said reverse osmosis unit contains a semipermeable membrane which is permeable to water and impermeable to saccharides and ethanol, whereby water diffuses through said membrane and is extracted from said residual liquid, said residual liquid being at a pressure of 50 to 100 atm abs. during said reverse osmosis step, and said second evaporator is at a temperature of from 25° C. to 65° C. and a pressure of less than 1 atm abs.

13. A process as claimed in claim 4, wherein said saccharide comprises one or more members of the group consisting of: glucose and sucrose.

14. A process as claimed in claim 4, wherein the ratio of the amount by weight per hour of said first fermented liquid discharged from said first fermenter to the amount by weight per hour of said second fermented liquid discharged from said second fermenter is at least 10.

15. A process as claimed in claim 4, wherein the ethanol concentration in said first fermenter is 8 wt. % or less.

16. A process as claimed in claim 4, wherein the water concentration of said residual fermented liquid fed from said first evaporator to said reverse osmosis unit is in the range of about 90 to 99 wt. %, and the concentration of water in said concentrated residual liquid after being subjected to reverse osmosis is in the range of 70 to 90 wt. %.

17. The process of claim 1 wherein said concentrated fermented liquid is fed to the first fermenter.

18. The process of claim 1 wherein said concentrated fermented liquid is fed to a second fermenter.

19. A process for the preparation of ethanol, which comprises:

in a fermentation zone, subjecting a fermentation liquid comprising a fermentable saccharide and water to a fermentation process, using an ethanol-producing microorganism, thereby to obtain a fermented liquid comprising ethanol, unreacted saccharide and water, said fermented liquid being substantially free of said microorganism; then feeding said fermented liquid into a first evaporator having a pressure of from 0.8 to 10 atmospheres absolute and having a temperature corresponding to the boiling point of said fermented liquid at said pressure thereby to evaporate, as vapor, a mixture of ethanol and water, said mixture having a high concentration of ethanol, and recovering from said first evaporator a first modified liquid comprising said unreacted saccharide, water and the remaining ethanol, then flowing said first modified liquid through a reverse osmosis unit and therein subjecting said first modified liquid to reverse osmosis conditions effective to separate from said first modified liquid a permeate fraction of water and recovering a second modified liquid comprising said unreacted saccharide, water and ethanol wherein the concentrations of said saccharide and ethanol in said second modified liquid are higher than the concentrations thereof in said first modified liquid; then feeding said second modified liquid into a second evaporator having a pressure of from 20 to 200 mm Hg and a temperature of from 25° to 65° C. whereby to separate, as vapor, a mixture of ethanol and water and to recover a third modified liquid having a high concentration of said unreacted saccharide; and subjecting said third modified liquid to a fermentation process.

* * * * *